United States Patent
Abahusayn

Patent Number: 5,934,902
Date of Patent: Aug. 10, 1999

[54] ORAL CLEANSING DEVICE

[76] Inventor: Mansur Abahusayn, 4432 Sandburg Way, Irvine, Calif. 92612

[21] Appl. No.: 09/061,681

[22] Filed: Apr. 16, 1998

[51] Int. Cl.⁶ .................................................. A61G 17/02
[52] U.S. Cl. ............................ 433/80; 601/162; 601/165
[58] Field of Search ............................. 433/80; 601/165, 601/162, 163, 164

[56] References Cited

U.S. PATENT DOCUMENTS

| | | | |
|---|---|---|---|
| 2,370,725 | 12/1945 | Gordon | 403/206 |
| 2,939,830 | 6/1960 | Green et al. | 204/248 |
| 3,669,274 | 6/1972 | Happ et al. | 210/222 |
| 3,680,705 | 8/1972 | Happ et al. | 210/222 |
| 4,108,167 | 8/1978 | Hickman et al. | 601/162 |
| 4,153,559 | 5/1979 | Sanderson | 210/222 |
| 4,229,634 | 10/1980 | Hickman et al. | 210/302 |
| 4,299,700 | 11/1981 | Sanderson | 210/222 |
| 4,299,701 | 11/1981 | Garrett et al. | 210/222 |
| 4,302,186 | 11/1981 | Cammack et al. | 433/80 |
| 4,326,954 | 4/1982 | Shroyer | 210/222 |
| 4,337,040 | 6/1982 | Cammack et al. | 433/80 |
| 4,428,837 | 1/1984 | Kronenberg | 210/222 |
| 4,430,785 | 2/1984 | Sanderson | 29/157 R |
| 4,682,584 | 7/1987 | Pose | 601/162 |
| 4,845,795 | 7/1989 | Crawford et al. | 15/22 R |
| 4,888,113 | 12/1989 | Holcomb | 210/222 |
| 4,933,088 | 6/1990 | Nishimura | 210/695 |
| 4,942,870 | 7/1990 | Damien | 433/80 |
| 4,989,590 | 2/1991 | Baum et al. | 128/66 |
| 5,029,576 | 7/1991 | Evans, Sr. | 433/80 |
| 5,095,893 | 3/1992 | Rawden, Jr. | 601/165 |
| 5,172,866 | 12/1992 | Ward | 239/446 |
| 5,189,751 | 3/1993 | Giuliani et al. | 15/22.1 |
| 5,220,914 | 6/1993 | Thompson | 601/165 |
| 5,263,218 | 11/1993 | Giuliani et al. | 15/22.1 |
| 5,286,192 | 2/1994 | Dixon | 433/80 |
| 5,305,492 | 4/1994 | Giuliani et al. | 15/176.1 |
| 5,341,534 | 8/1994 | Serbinski et al. | 15/22.1 |
| 5,378,153 | 1/1995 | Giuliani et al. | 433/216 |
| 5,383,242 | 1/1995 | Bigler et al. | 15/22.1 |
| 5,399,089 | 3/1995 | Eichman et al. | 433/80 |
| 5,435,034 | 7/1995 | Bigler et al. | 15/22.1 |
| 5,465,444 | 11/1995 | Bigler et al. | 15/22.1 |
| 5,637,226 | 6/1997 | Adam et al. | 210/695 |
| 5,755,572 | 5/1998 | Bab et al. | 433/80 |

*Primary Examiner*—John J. Wilson
*Assistant Examiner*—Patrick A. Hilsmier
*Attorney, Agent, or Firm*—Curtis L. Harrington

[57] ABSTRACT

The oral cleansing device assembly is an oral hygiene tool which relies upon weak strength and small sized magnets in order to effect a change in the resonance and/or polarity of the water molecules such that the water is effective for cleaning debris, scale, and plaque from the teeth, gums, tongue, and oral cavity in general. The oral cleansing device assembly has a non-metallic housing which contains the magnets and tubing through which water passes when the device is in operation; the housing also doubles as a handle. The oral cleansing device assembly has jet-tips for discharging the water into an oral cavity; the jet-tips are attachable to a quick-connector within the housing of the oral cleansing device assembly. The oral cleansing device assembly is ideal and safe to use for any adult or child who seeks to avoid exposure to electromagnetic fields and who wishes to avoid use of high water pressure in their mouth care routine. The oral cleansing device assembly is a user-friendly alternative for mouth care and hygiene, and is effective at removing unwanted debris, plaque, and scale from the mouth, teeth, gums, and tongue, resulting in fresher breath and improved dental health.

15 Claims, 3 Drawing Sheets

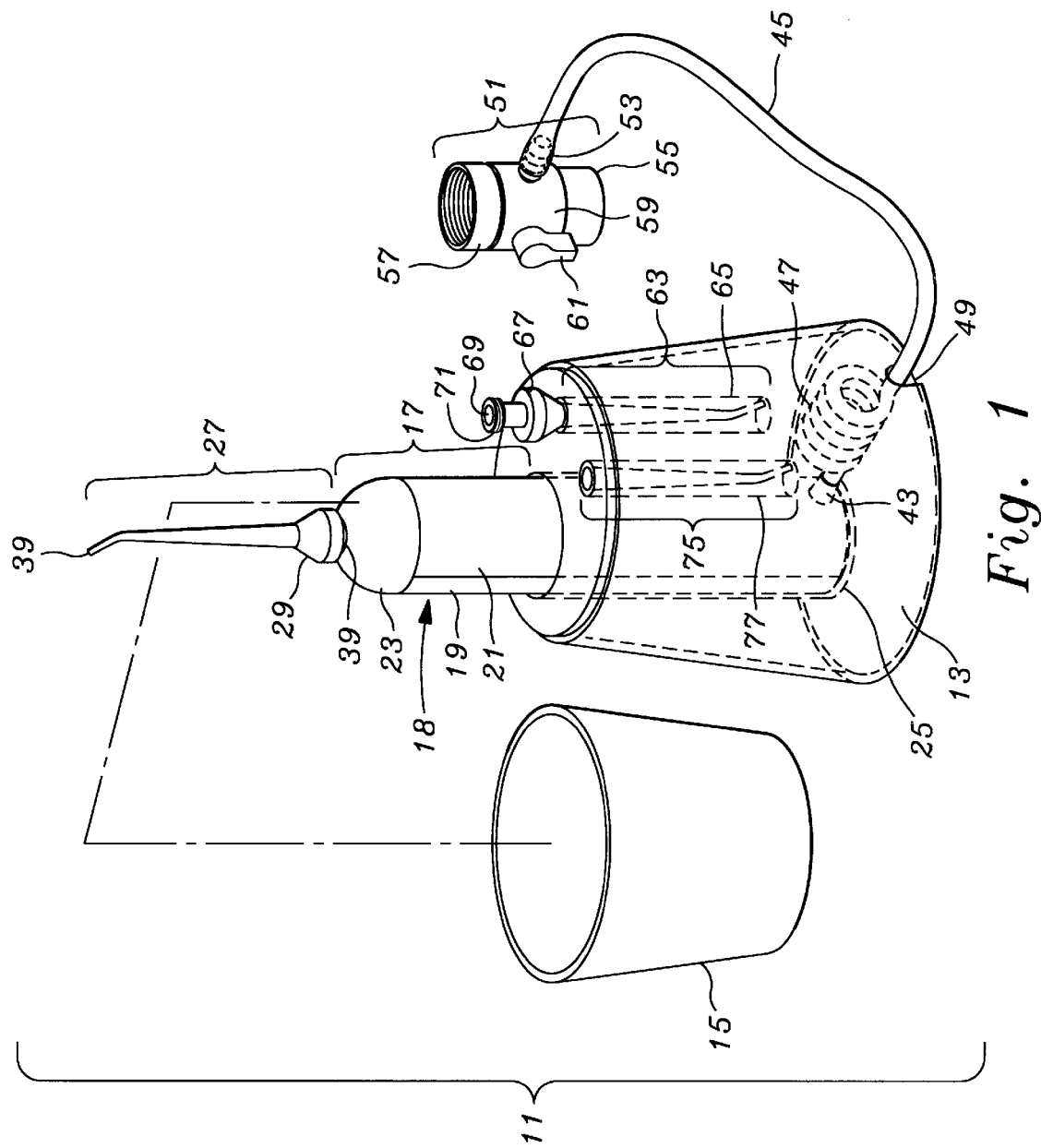

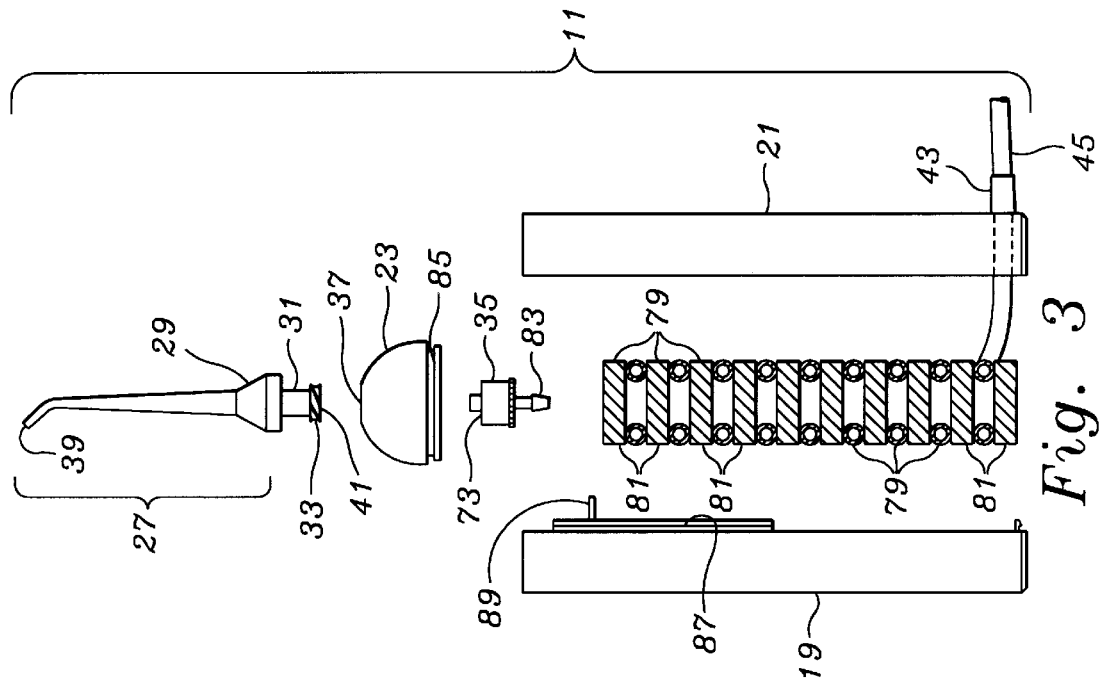
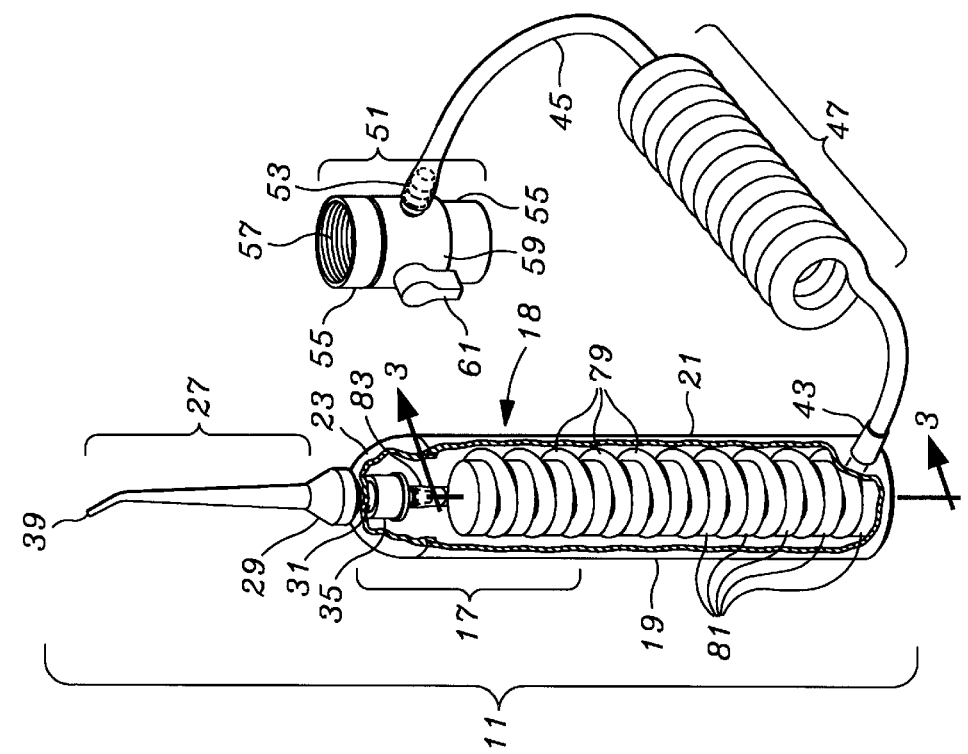

ORAL CLEANSING DEVICE

FIELD OF THE INVENTION

This invention relates to the field of oral cleansing devices, and more specifically to a device which facilitates oral cleansing by way of a constant or intermittent jet stream of water which has been subjected to a magnetic field.

BACKGROUND OF THE INVENTION

Other devices currently exist and are available which perform the function of oral cleansing by way of a variable pressure stream of fluid. These devices are designed to cleanse the mouth using water pressure to irrigate food and other debris from between the teeth and gums. One of the best known devices currently on the market is the WATER-PIK oral irrigator (U.S. Pat. Nos. 4,302,186; 4,229,634; 4,337,040; and 4,989,590). Most WATERPIK systems make use of electricity in order to power an internal pump. Once the pump is activated, water or other liquid is extracted from a reservoir and ejected at relatively high pressure in order to flush particulate matter from the teeth and gums. The reservoir is included with the WATERPIK system, and is designed to hold enough water or other cleaning fluid to last through several cleanings using the WATERPIK system. Although the WATERPIK is a popular and effective oral cleansing device, use of the WATERPIK system's motor creates undesirable electromagnetic fields. In addition, the WATERPIK system must use electricity in order to function, and a user may not always be near a source of electricity of the correct voltage. Another potential problem with this system is that the leftover liquid in the reservoir may become stagnant between cleanings, proving to be somewhat unsanitary. In order to maintain the integrity of cleanliness in a WATERPIK system, a user must change the liquid frequently or must fill the reservoir with fresh water or cleaning fluid immediately prior to each use. Either of these options is inconvenient and time consuming, and may prove to be somewhat wasteful if a fluid other than water is used. Another potential problem with the WATERPIK system is the possibility of extremely high water pressure being delivered to a user's delicate gum tissue and oral cavity. Although some models of the WATERPIK system has a dial by which a user may adjust the pressure at which fluid is ejected, there is potential for the dial to become maladjusted; a user may also overestimate the desired pressure, thereby delivering a stream of fluid that may cause injury and bleeding gums. Another conceivable problem with the WATERPIK system may occur if children have access to the system; medium to high pressure streams of cleaning fluid may certainly cause damage the tender gums or teeth of a child. What is therefore needed is an oral cleansing device which operates independently of electricity, which is safe and gentle yet effective for oral cleansing and hygiene of both adults and children, and which uses a fresh supply of water for each episode of oral cleansing without extra effort on the part of a user.

SUMMARY OF THE INVENTION

The oral cleansing device of the present invention operates independently of electricity and uses water flow and pressure from an ordinary household tap in order to achieve oral cleansing. The oral cleansing device has an internally threaded female connector or diverter which facilitates coupling of the oral cleansing device with threads which are present on most household faucets. An adapter included can accommodate most threads. The diverter includes a three-way, flow control valve that may be adjusted via a lever which is located on the outer surface of the diverter. The purpose of the flow control valve is to control the stream of water which exits the tip of the oral cleansing device to the desired pressure. When the valve is in the closed position, flow is absent in the device, but faucet flow is not interrupted. In the open position, the flow of water is at full strength and full pressure; the intermediate position results in a low to medium strength flow of water. Because the oral cleansing device of the present invention does not rely on extra water pressure to do an effective job of oral cleansing, both the high and medium pressure settings of the oral cleansing device are at relatively reasonable and extremely safe levels, and are unlikely to cause any injury to teeth, gums, or oral cavity. A first, straight portion of a length of tubing through which the water flows when the device is in operation is joinable with a graduated projection situated on a lateral side of the threaded diverter; the tubing has a first, coiled section for ease of retraction; the tubing has a second, straight portion which enters the bottom of the housing of the device. The portion of the tubing which is located within the housing of the device is coiled; each turn of the coils winds a major portion of a turn between an adjacent pair of a series of mutually magnetically attractive, parallel, disc magnets. The housing is preferably a ceramic counter top housing for the stationary model, and without the housing, the device is easily portable. The magnets are situated in a stacked configuration within the housing of the device. The housing of the device is preferably constructed of plastic or other non-metallic material, is sized and shaped so that it may be easily gripped and manipulated by a user as a handle, and further serves to firmly and radially hold in place the system of magnets and coiled tubing. The tubing terminates within the housing at a second graduated projection which is positioned on the bottom end of a quick-connector located just within the domed portion of the upper end of the housing. The domed portion of the housing has an opening at the top center such that the quick-connector within the domed portion may accept an tapered jet-tip through the opening in the dome. The jet tip has an orifice at each end, the smaller of which is at the far end of the jet tip and is the exit point for the water flowing through the system. The tapered jet-tip is of a length and narrowness which allows for insertion into and easy movement about an oral cavity. The tapered jet-tip further has an angled portion near its far end in order to facilitate access to areas of the oral cavity which may be difficult to reach. The oral cleansing device is designed to remove scale, plaque, stains and particles from the teeth, gums and mouth, the removal of which results in fresher breath and healthier teeth and gums for a user. The oral cleansing device is also useful for gum massage, which may reduce the risk of gingivitis. Directed at the tongue, the oral cleansing device removes odor causing bacteria, allowing a cleaner mouth and avoiding stale, offensive breath. The oral cleansing device uses the pressure of standard household plumbing to produce the fresh stream of water which exits from the jet-tip. Electricity is not necessary in order to operate the device of the invention. The device of the invention relies upon a series of small magnets which are relatively weak and therefore very safe. As water passes through the tubing system, it flows between the pairs of magnets in a path which perpendicularly crosses the magnetic fields created by adjacent pairs of the series magnets; this particular treatment of the water imparts scale and debris removing capabilities to the water itself. The distance of travel of the water through the field of magnetic flux has to be substantial for the water to gain these scale-removing capabilities. In order to increase the duration of exposure of the water to the magnetic field of the magnets, the tubing has loops to increase the extent of exposure to the magnet system. The magnets in this device have been carefully positioned such that the distance between magnets is as small as possible yet still safe and effective for treating the water. The configuration of the tubing and magnets in the oral cleansing device allows the water maximum exposure to the magnetic fields while preserving the safety of the system by use of small magnets.

BRIEF DESCRIPTION OF THE DRAWINGS

The invention, its configuration, construction, and operation will be best further described in the following detailed description, taken in conjunction with the accompanying drawings of a first embodiment of the present invention in which:

FIG. 1 is a view of the oral cleansing device of the present invention as assembled with all parts in their respective places within a storage unit for the device; FIG. 1 illustrates the storage unit for the device with a covering lid/drinking cup removed;

FIG. 2 illustrates the oral cleansing device of the present invention with a portion of the housing of the device shown broken away; FIG. 2 illustrates the coiled tubing and magnet system within the housing of the device;

FIG. 3 is an exploded view, but illustrating a cross sectional view of the central magnet and coil portion of the oral cleansing device of the present invention taken along line 3—3 of FIG. 2, and more clearly illustrates the coiled tubing and magnet arrangement within the housing of the device as well as the quick-connector relative to the domed portion of the housing and the jet-tip.

DETAILED DESCRIPTION OF THE DRAWINGS

Figure 4:
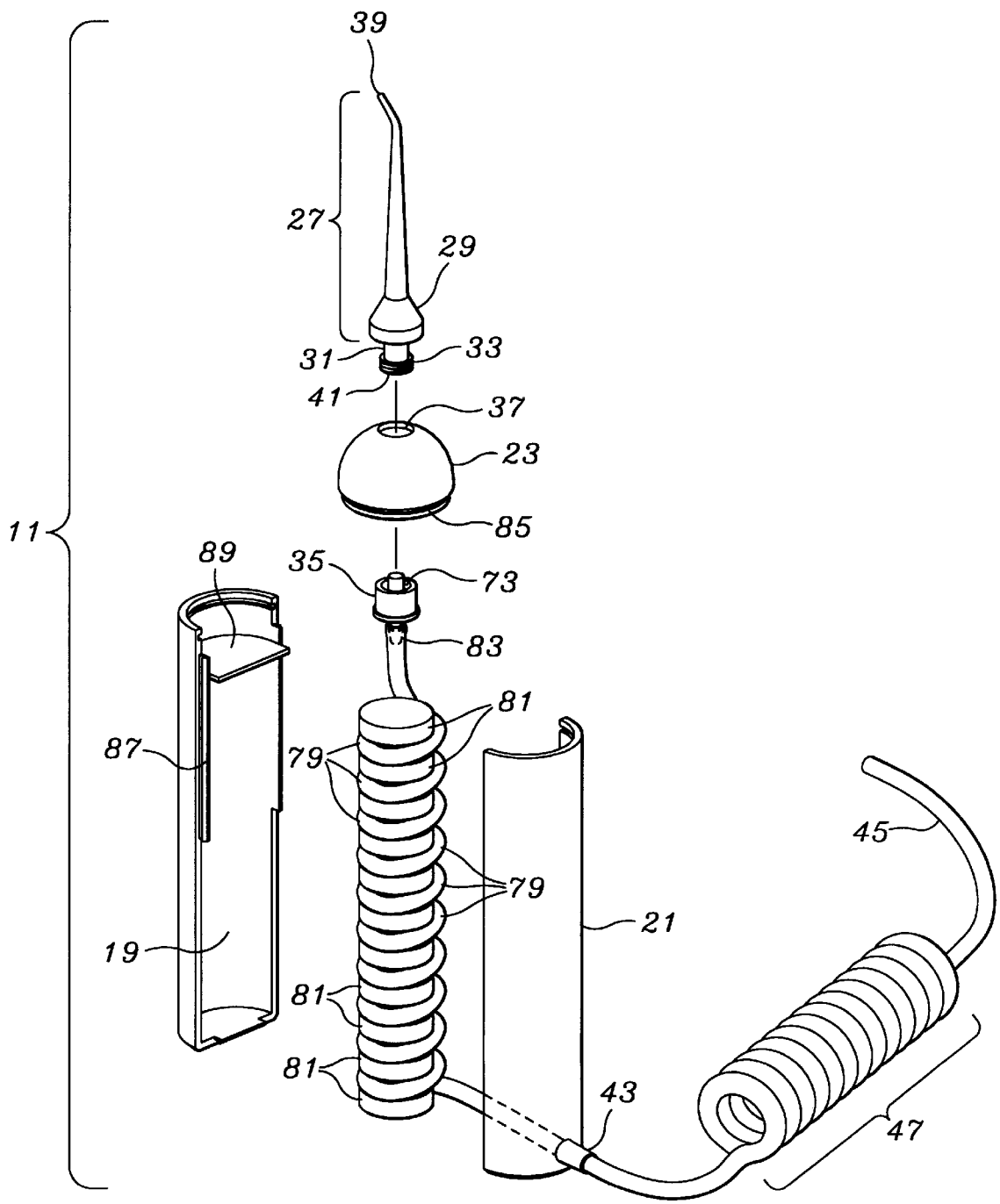
FIG. 4 is an exploded view of the oral cleansing device of the present invention which clearly illustrates the position of the tubing relative to the magnets within the housing of the device, and illustrates the position of the jet-tip relative to the domed portion of the housing and the quick-connector.

FIG. 1 is a view of the oral cleansing device assembly 11 of the present invention as having a storage unit 13 which has a removable lid 15. The removable lid 15 serves to protect the oral cleansing device assembly 11 from airborne germs and dust when not in use, and can also double as a drinking or gargling cup. FIG. 1 illustrates the storage unit 13 for the oral cleansing device assembly 11 with the removable lid 15 to one side and inverted. The oral cleansing device assembly 11 supports a hand held wand assembly 17 having a housing 18 which is approximately 1⅛ inches in diameter and which consists of three components: a first side portion 19, a second side portion 21 and a domed end portion 23. The wand assembly 17 of the oral cleansing device assembly 11 is illustrated resting within a large compartment 25 of the storage unit 13. Adjacent the domed end portion 23 of the housing 18 is a tapering flow conduit or jet-tip 27 with a manually graspable, removably attachable base 29 having a male end 31 (not shown, see FIG. 3) with a raised land 33 which is connectable by snap-fit to a quick-connector 35 (not shown, see FIGS. 2–4) through a central aperture 37 in the domed end portion 23. The jet-tip 27 is approximately 2¾ inches in length, is hollow, and has a small orifice 39 at its far end and a larger orifice 41 (see FIG. 3) at its base. The width of the jet-tip 27 is approximately 7/16 inch at its base and tapers to approximately 3/16 inch at the far end. The small orifice 39 of the jet-tip 27, has a diameter of approximately 1/32 inch, and is the site where water exits the oral cleansing device assembly 11. The removably attachable base 29 of the jet-tip 27 allows connection of the jet-tip 27 with the quick-connector 35 (see FIGS. 2 and 3) just inside the domed end portion 23 of the wand assembly 17. The wand assembly 17 of the oral cleansing device assembly 11 has an open passage 43 at its base through which a tubing 45 passes. The tubing 45 for use with the oral cleansing device assembly 11 is preferably constructed of a flexible, chemically inert tubing material, except in areas where water supplies are fluorinated. Use of the oral cleansing device assembly 11 in areas where water supplies are fluorinated would require that the tubing 45 be constructed from a material which is nonreactive with fluoride. The tubing 45 will ideally have an inner diameter of approximately 3/32 inch and an outer diameter of approximately 3/16 inch. The tubing 45 has a first coiled section 47 which allows a user to retract the oral cleansing device assembly 11 from the storage unit 13 with ease. The tubing 45 passes through a opening 49 at the base of the storage unit 13 and connects to a female coupler or diverter 51 at a graduated projection 53 on the outer surface of the diverter 51. The diverter 51 has a sleeve 55 which has an internally threaded surface 57 compatible with threads found on most ordinary household faucets (not illustrated). An adapter is included but not shown, which will accommodate most faucets. The diverter 51 has an main body 59 rotatable about the sleeve 55. The rotation of the main body 59 about the sleeve 55 allows a user to move the oral cleansing device assembly 11 about without stressing or kinking the tubing 45. The diverter 51 contains a three way valve (not illustrated) which is controlled by a lever 61 located on the outer surface of the diverter 51. The lever 61 (and thus the three way valve) has a first, open position; a second, intermediate position; and a third, closed position. Though not illustrated, each position of the lever 61 may be well marked on the exterior surface of the diverter 51. The lever 61 is used to adjust the valve (not illustrated) for control of water flow through the tubing 45. FIG. 1 illustrates a first, auxiliary jet-tip 63 for use with the oral cleansing device assembly 11 wand assembly 17 which is identical to the jet-tip 27 illustrated adjacent the domed end portion 23 of the wand assembly 17 of the oral cleansing device assembly 11. The first, auxiliary jet-tip 63 is illustrated as inverted within a first, small compartment 65 in the storage unit 13. FIG. 1 best illustrates the larger orifice 41 of the jet-tip 27, which is identical to the one seen at the base of the first auxiliary jet-tip 63. The first auxiliary jet-tip 63 also has a manually graspable, removably attachable base 67 which is directly connectable to the quick-connector 35 (see FIG. 2) by snap-fit. The base 67 of the first auxiliary jet-tip 63 also has a male end 69 with a raised land 71 which snap-fits into an annular depression 73 in the top of the quick-connector 35 (not yet shown-see FIG. 4). FIG. 1 illustrates a second auxiliary jet-tip 75 within a second small compartment 77 in the storage unit 13; the second auxiliary jet-tip 75 is shown by itself; however, the second auxiliary jet-tip 75 would normally include a removably attachable component such as 29 or 67 and is shown detached for illustration purposes only. Multiple jet-tips such as 27 and 63 are available for use with the oral cleansing device assembly 11 of the present invention in order that each user may have their own jet-tip 27, 63 for hygiene and cleanliness purposes, and will be preferably color coded for ease of identification. The removably attachable component 29, 67 of each jet-tip 27, 63 allows for disassembly of the jet-tip 27, 63 for convenience in cleaning and inspection.

FIG. 2 is an illustration of the flowing portion of the oral cleansing device assembly 11 and illustrates a segment of each of the first side portion 19, the second side portion 21 and the domed end portion 23 of the wand assembly 17 broken away. FIG. 2 illustrates a second coil 79 in the tubing 45 which is within the housing 18; the second coil 79 in the tubing 45 is arranged such that a significant portion of its length lies between adjacent pairs of the series of magnets 81. As the water flows through the oral cleansing device assembly 11 and through the second coil 79 in the tubing 45 between pairs of the magnets 81, it perpendicularly crosses magnetic field lines (not visible) which are created by the magnet pairs 81. Subjecting the water to this path of flow between the magnet pairs 81 causes a change in the resonance and/or polarity of the water molecules such that the water has de-scaling capabilities as a result. FIG. 2 illustrates the quick-connector 35 housed within the domed end portion 23 of the housing 17; FIG. 2 also illustrates the second coil 79 of the tubing 45 as attached to a second graduated projection 83 which is on the underside of the quick-connector 35.

FIG. 2 illustrates the quick-connector 35 as attached to the jet-tip 27 through the domed end portion 23 of the housing 18 by direct, snap-fit connection between the male end 31 of the jet-tip 27 and the removably attachable base 29. FIG. 2 also illustrates the open passage 43 in the second side portion 21 of the wand assembly 17 through which the tubing 45 passes. The first coiled section 47 of the tubing 45 is illustrated, and the tubing 45 is connected to the diverter 51 by a graduated projection 53 on the outer surface of the main body 59 of the diverter 51. Also visible in FIG. 2 is the internally threaded surface 57 of the diverter 51 and the lever 61 which is used to control the flow of water through the oral cleansing device assembly 11.

FIG. 3 is an exploded, cross-sectional view of the oral cleansing device assembly 11 of the present invention as taken along line 3—3 of FIG. 2. FIG. 3 more clearly illustrates the removably attachable base 29 of the jet-tip 27 which is connectable directly to the quick-connector 35 through the central aperture 37 in the domed end portion 23 of the housing 18. A clearer illustration of the raised land 33 of the male end 31 of the removably attachable base 29 is present in FIG. 3. The removably attachable base 29 and thus the jet-tip 27 may be easily snapped into or out of the quick-connector 35 for quick insertion and removal. Ease of insertion and removal of the jet-tip 27 and the removably attachable base 29 facilitates use of the oral cleansing device assembly 11 by multiple users with very little or no trouble. Exchange of the jet-tip 27 by each user and replacement with a user's personal jet-tip 27 prior to use ensures sanitary and safe use of the oral cleansing device assembly 11 and prevents transmission of germs and diseases.

FIG. 3 further illustrates a lipped rim 85 on the domed end portion 23 of the first and second side portions 21 and 23 of the housing 18 which helps to hold the domed end portion 23 in place once the wand assembly 17 of the oral cleansing device assembly 11 is assembled. FIG. 3 more clearly illustrates the stacked arrangement of the second coil 79 of the tubing 45 as it winds in a looped fashion between the magnets 81 within the housing 17. The relationship of the first side portion 19 of the housing 17 to the second side portion 21 is more apparent in FIG. 3. The first side portion 19 is compatible with the second side portion 21 and has a pair of elongate, snap-fit members 87 which allow for connection of the first side portion 19 with the second side portion 21. It is clear from the illustration in FIG. 3 that the first side portion 19 and second side portion 21 of the housing 17 fit together with the domed end portion 23 to surround a stack comprised of the second coil 79 of tubing 45 and the magnet pairs 81 during normal assembly and use of the wand assembly 17. The purpose of the housing 18 is two-fold: the first side portion 19 and second side portion 21 restrict lateral movement of the stack formed by the magnet pairs 81 and second coil 79 of tubing 45 when the unit is assembled. The first side portion has a ledge 89 on its inner surface which is positioned directly atop the stack of tubing 45 and magnet pairs 81 and serves to restrict their vertical movement when the components of the housing 18 are assembled. The second purpose of the housing 18 is to provide the user a place to grip the wand assembly 17 while operating the device. FIG. 3 also illustrates in detail the second graduated projection 83 to which the second coil 79 of the tubing 45 would normally be attached.

Also illustrated in FIG. 3 is the open passage 43 at the base of the second side portion 21 of the housing 17 through which the tubing 45 passes.

FIG. 4 is an exploded view of the wand assembly 17 of the present invention and illustrates the jet-tip 27 with removably attachable base 29 attached. The raised land 33 on the male end 31 of the removably attachable base 29 is illustrated adjacent the central aperture 37 in the domed end portion 23 of the housing 17. The lipped rim 84 interior to the outer edge of the domed end portion 23 of the housing 17 is adjacent the quick-connector 35. The annular depression 73 in the upper surface of the quick-connector 35 into which the male end 31 of the removably attachable base 29 would normally be inserted is clearly illustrated in FIG. 4. The quick-connector 35 is illustrated with the second coil 79 of tubing 45 attached thereon. The second graduated projection 83 is illustrated in phantom within the end of the attached tubing 45. The second coil 79 of tubing 45 loops around and between the attractive magnet pairs 81. FIG. 4 illustrates the first side portion 19 of the housing 17, and more clearly illustrates the ledge 89 which is situated within the first side portion 19 and which acts to somewhat compressably secure the stack of tubing 45 and magnet pairs 81 when the unit is assembled. The elongate, snap-fit members 87 on the first side portion 19 of the housing 17 is more readily visible in FIG. 4.

FIG. 4 illustrates the second side portion 21 of the housing 17 with the open passage 43 though which the tubing 45 exits the housing 17 of the oral cleansing device assembly 11. FIG. 4 illustrates the first coiled section 47 of the tubing 45 which allows for retraction of the oral cleansing device assembly 11 from the storage unit 13 upon usage.

The present invention is ideal for use in most households having threaded faucets to which the oral cleansing device assembly 11 may be attached. The oral cleansing device assembly 11 is a safe and effective alternative to devices which are currently available for oral hygiene. The oral cleansing device assembly 11 provides a user with a natural way to cleanse the mouth, teeth, and gums without the possibility of damage to delicate mouth and gum tissue and without exposure to electromagnetic fields that may be encountered using a device which may currently be on the market. The oral cleansing device assembly 11 is safe for both adult users and children alike since the oral cleansing device assembly 11 does not rely on high water pressures to do an effective job of oral cleansing. The oral cleansing device assembly 11 may also be a fun way for parents to motivate and encourage children to engage in mouth care that might otherwise be considered a chore.

Although the present invention has been derived with reference to particular illustrative embodiments thereof, many changes and modifications of the invention may become apparent to those skilled in the art without departing from the spirit and scope of the invention. Therefore, included within the patent warranted hereon are all such changes and modifications as may reasonably and properly be included within the scope of this contribution to the art.

What is claimed:

1. An oral cleansing device assembly comprising:
   a housing;
   a plurality of axially aligned planar magnets having a curving outer periphery enclosed by said housing and oriented to facilitate a magnetic field;
   a length of hollow tubing having a portion of said tubing enclosed by said housing and within said magnetic field and passing between each one of said plurality of magnets and another one of said plurality of magnets, said length of hollow tubing having a first end and a second end, the magnetic field oriented substantially at right angles to a major extent of said tubing;
   a connector for connecting said first end of said hollow tubing to a fluid source; and
   a member adjacent said housing and attachable to said second end of said hollow tubing for discharging said fluid from said hollow tubing of said oral cleansing device assembly into the oral cavity of a user.

2. The oral cleansing device assembly recited in claim 1 wherein said plurality of magnets are disk shaped.

3. The oral cleansing device assembly recited in claim 1 wherein said hollow tubing comprises at least one coiled section.

4. The oral cleansing device assembly recited in claim 3 wherein said coiled section has at least one turn and a majority of said turn extends between two of said plurality of magnets along the radial inside of said curving outer periphery.

5. The oral cleansing device assembly recited in claim 4 wherein said connector includes a control adjustable between at least 2 flow control positions for controlling flow of said fluid from said fluid source.

6. The oral cleansing device assembly recited in claim 4 wherein said member for ejecting fluid from said oral cleansing device assembly is a tapering flow tube.

7. The oral cleansing device assembly recited in claim 6 wherein said tapering flow tube is attached to said hollow tubing by an intermediate connector attached to said housing.

8. The oral cleansing device assembly recited in claim 7 wherein said intermediate connector comprises a body having a first end and a second end and an aperture extending therethrough; a first end of said body having an annular depression therein; and a second end having a projection joinable with said hollow tubing.

9. The oral cleansing device assembly recited in claim 8 wherein said tapering flow tube further comprises an annular male member complementary to said annular depression in said first surface of said intermediate connector, and interfittable therewith.

10. The oral cleansing device assembly recited in claim 6 wherein said housing comprises at least a first and a second joinable hemi cylindrical sections.

11. The oral cleansing device assembly recited in claim 10 and further comprising a third section joinable at an end of with said first and second sections joined hemi cylindrical sections, said third section having an aperture therethrough.

12. The oral cleansing device assembly recited in claim 1 wherein said connector is attachably connectable to a faucet.

13. An oral cleansing device assembly comprising:
    a hollow handle;
    a plurality of magnets enclosed by said hollow handle;
    a hollow tubing partially enclosed by said hollow handle and in contact with said plurality of magnets;
    a connector for connecting said hollow tubing to a fluid source; and
    a jet-tip attachable to said hollow tubing and supported by said hollow handle for ejecting fluid from said oral cleansing device assembly.

14. The oral cleansing device assembly recited in claim 13 and further comprising a storage unit.

15. The oral cleansing device assembly recited in claim 13 and further comprising a plurality of jet-tips.

* * * * *